United States Patent [19]

Wong

[11] Patent Number: 4,625,278
[45] Date of Patent: Nov. 25, 1986

[54] METHOD AND APPARATUS FOR ENHANCING CRT SCREEN MARKINGS IN A PHYSIOLOGICAL DISPLAY SYSTEM

[76] Inventor: Alan S. Wong, 1238 Via Rancho Pkwy., Escondido, Calif. 92025

[21] Appl. No.: 534,748

[22] Filed: Sep. 22, 1983

[51] Int. Cl.⁴ .......................... A61B 5/04; G06F 3/14
[52] U.S. Cl. ................................... 364/417; 364/415; 128/711; 128/712; 350/709; 350/723
[58] Field of Search ................ 128/711, 712; 340/709, 340/723; 364/415, 417

[56] References Cited

U.S. PATENT DOCUMENTS

| | | | |
|---|---|---|---|
| Re. 29,921 | 2/1979 | Cherry et al. | 128/711 X |
| 3,858,034 | 12/1979 | Anderson | 364/417 |
| 4,072,851 | 2/1978 | Rose | 364/487 |
| 4,093,995 | 6/1978 | Smith et al. | 340/750 X |
| 4,483,347 | 11/1984 | Wong | 128/712 |
| 4,495,491 | 1/1985 | Postl | 340/709 |
| 4,528,988 | 7/1985 | Wong | 128/712 |

Primary Examiner—Jerry Smith
Assistant Examiner—Charles B. Meyer

[57] ABSTRACT

Enhancement of marking symbols indicative of abnormal ECG beats displayed on a CRT storage tube may be effected by periodic revivification. An arrhythmia computer is utilized to detect and classify the abnormal beats-and their location is marked by a symbol generated by a character generating circuit. Visual enhancement is effectuated by periodically resetting the character generator in accordance with the desired refresh repetition rate.

9 Claims, 5 Drawing Figures

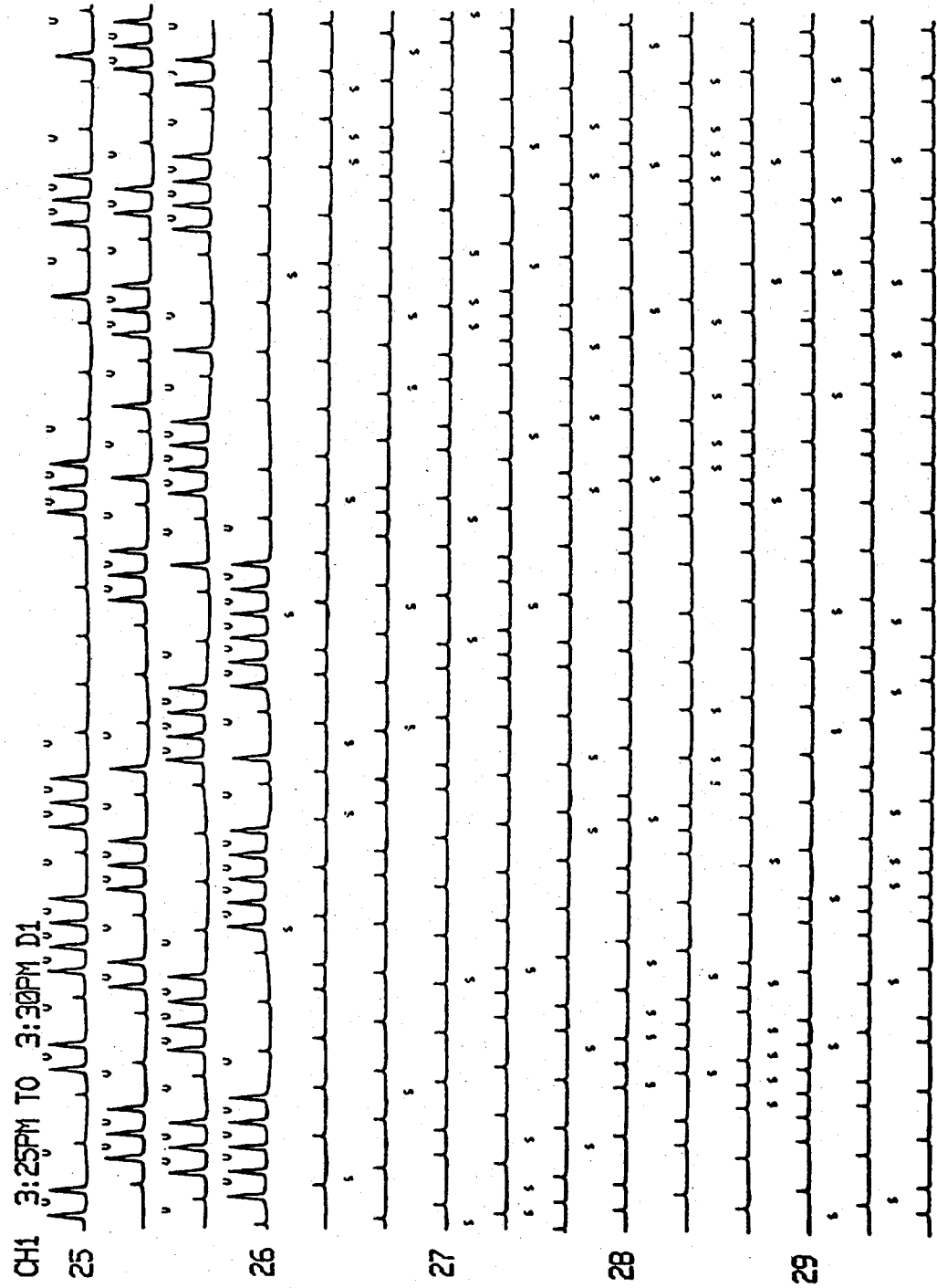

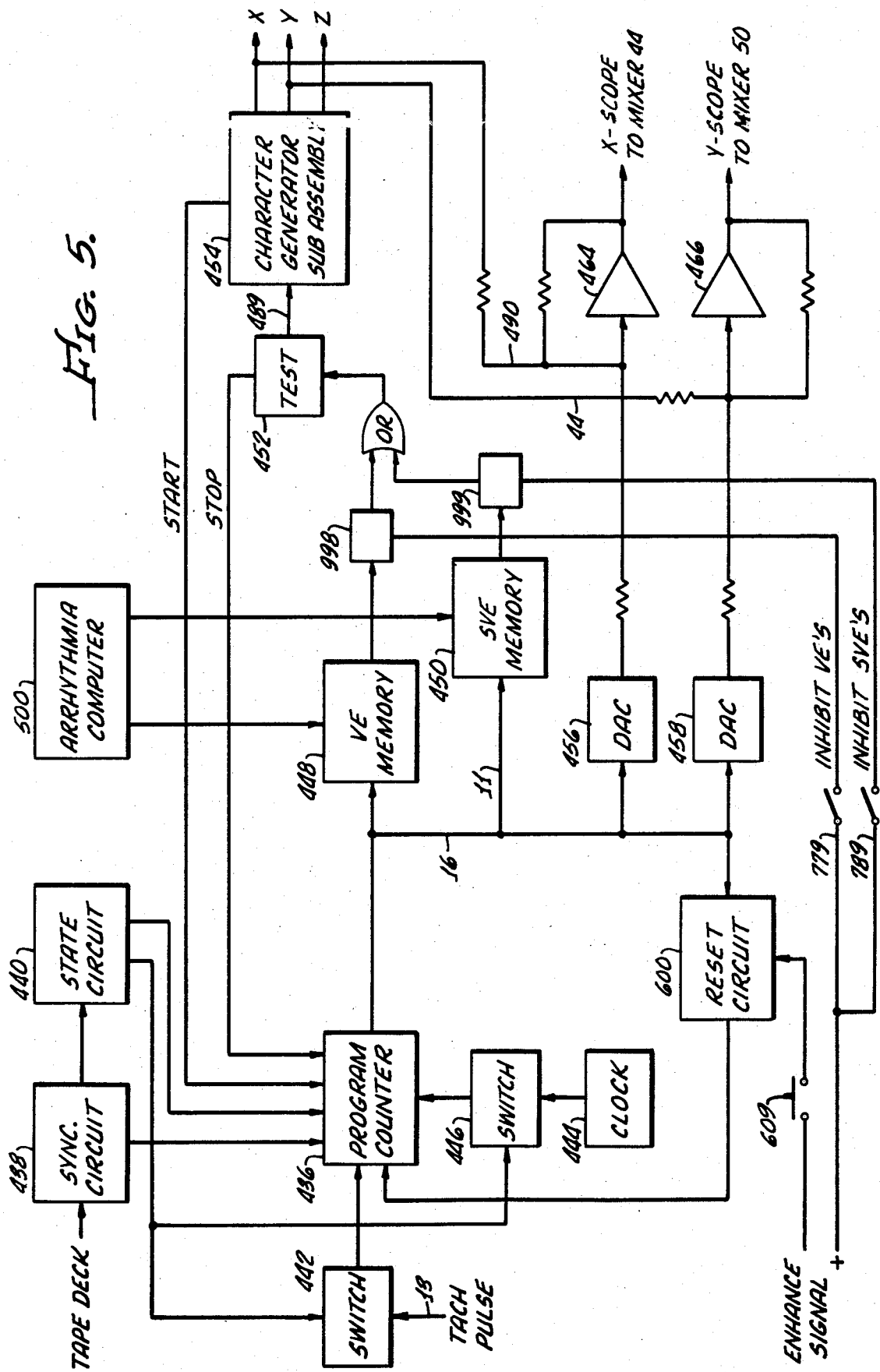

METHOD AND APPARATUS FOR ENHANCING CRT SCREEN MARKINGS IN A PHYSIOLOGICAL DISPLAY SYSTEM

BACKGROUND OF THE INVENTION (A) Field of the Invention

The invention relates generally to Physiological display systems and more particularly to CRT storage tube devices that are utilized to display electrocardiographic signals which have been processed and categorized by computer analysis into normal and abnormal beats. The electrocardiographic signals (ECG) result from electrical currents that circulate upon the skin surface as a result of the expansions and contraction of the cardiac muscle (heart). The ECG signals are useful to the clinical physician since certain known and identifiable abnormalities are known to produce particular waveform irregularities. These irregularities however, may occur infrequently, or intermittently, and their occurence may depend upon the patients' stress or activity. It is thus desirable to accumulate large volumns of continuous data during times when the patient is engaged in carrying out his normal day to day activities. For this purpose, a small compact tape recorder is worn by the patient as he performs his usual functions. The recorded tape can be taken to a laboratory and rapidly replayed analyzed, and formatted for display. During the analysis, abnormal beats may be categorized and marked for identification.

(B) Description of the Prior Art

The expansion and contraction of the cardiac muscle produces surface skin electrical signals which can be recorded and analyzed to determine the condition of the heart. Of interest to the physician is an analysis of continuously recorded signals over an extended period particularly during the normal day to day activities of the patient. Known types of anomalous signals that represent arrhythmic (irregular variations in rhythm) and ectopic (ventricular ectopic and superventricular beats) activity can then be identified and treatment prescribed.

The analysis is accomplished by recording the ECG signals in real time on a small compact tape recorder which is worn by the patient as he carries out his daily activities. The recorded ECG signals are then processed by replaying the signals on a cathode-ray oscilloscope. One particular type of prior art replay in fast time utilizes the superposition of predecessor complexes and is known as an AVSEP® display. An example of a system which may be used for the recording and playback of ECG signals with the recording in real time and with the playback in fast time, reference is made to U.S. Pat. No. 3,215,136, issued Nov. 2, 1965 in the name of Norman J. Holter, et. al.

An extension of the prior art ECG scanning device described above, an improvement as shown in U.S. Pat. No. 3,718,772, issued on Feb. 27, 1973 in the name of Clifford Sanctuary, discloses a display system wherein recording is carried out at a very slow speed on a single tract with subsequent playback at a high speed so as to visually superpose a plurity of waveforms on an oscilloscope. A further extension of the prior art is shown in U.S. Pat. No. 4,006,737 filed Jan. 4, 1974 by Issac Raymond Cherry for a scanning device for the processing and presentation of simultaneous ECG data from at least two pairs of leads located in different positions on the patient.

Of particular interest with respect to the present invention is U.S. patent application, Ser. No. 356,326 by Alan S. Wong, filed Mar. 10, 1982, entitled, "An Improved Method and Apparatus for Displaying Electro-Cardiographic Signals" and U.S. patent application No. 06/510,677 by Alan S. Wong, filed July 5, 1983 entitled "Physiological Display System", both of which are hereby cross referenced to this application, the contents of which are referred to as background information relative to and for the purpose of understanding the present disclosure. In both of these applications, the physiological waveform is traced on a CRT storage tube, along with the time of day and patient information. Ser. No. 356,326 teaches how the display is marked to identify those physiological events which have been detected by the system as being abnormal. By tracing the first-channel during a first-sweep while storing the second-channel within a memory for use during the second-sweep, two independent channels of physiological data may be displayed on alternate rows. Various display formats may be selected by the operator, the operational modes being determined by command signals operable coupled to program counters which sequentially step through various memories devoted to the storage of the digitized physiological signals to be converted to analog for display. In Ser. No. 356,326, the display format is typically a two dimensional array comprised of successive lines of continuous waveforms as measured in time, beginning at the top of the CRT storage tube and proceeding from left to right and from top to bottom in time. After completion, ectopic events are recognized and corrolated with their time of occurence, and a subsequent sweep is generated so as to place small markers adjacent to those abnormalities which are identifiable as constituting at predetermined deviation from the norm. It will be understood that it is desirable to minimize the size of the markers to avoid cluttering, particularly where a large amount of real time data is to be played on a single frame. It will also be evident however, that small markers are difficult to observe. What is actually desired is a system for emphasizing small markers so that they can be easily identified.

Accordingly, a primary object of the invention is to provide a physiological display system wherein abnormal events are identified by markers having a visual characteristic which distinguishes the markers from the displayed physiological data.

A further object of the invention is to provide an apparatus which periodically refreshes selected aspects of a storage tube display.

A further object of the invention is to provide refresh signals to cause selected portions of a storage tube display to "blink" in accordance with the refresh signal rate.

Other objects and advantages of the present invention will be obvious from the detailed description of a preferred embodiment given herein below:

SUMMARY OF THE INVENTION

The aforementioned objects are realized by the present invention which comprises an arrhythmia computer for detecting and classifying abnormal ECG beats, a character generating circuit for writing a particular abnormal marking symbol, a CRT storage tube for displaying ECG data and abnormal marking symbols in accordance with a plurality of cartesian array formats wherein time is measured along the horizontal axis and the amplitude of the ECG signal appears as vertical excursions, a memory for storing the location of each abnormal marking symbol in relation to the displayed data and a program counter which repetitively sequences through each address of the memory and X, Y and Z axis drive circuitry responsively coupled to respond to the analog voltages from the character generator, for periodically refreshing the marking symbols.

DESCRIPTION OF THE DRAWINGS

FIG. 4 is a preferred 60 minute format with annotation and waveform data illustrating abnormal ECG marking signals.

FIG. 5 shows a block diagram of the symbol marking system.

DETAILED DESCRIPTION OF A PREFERRED EMBODIMENT

Figure 1:
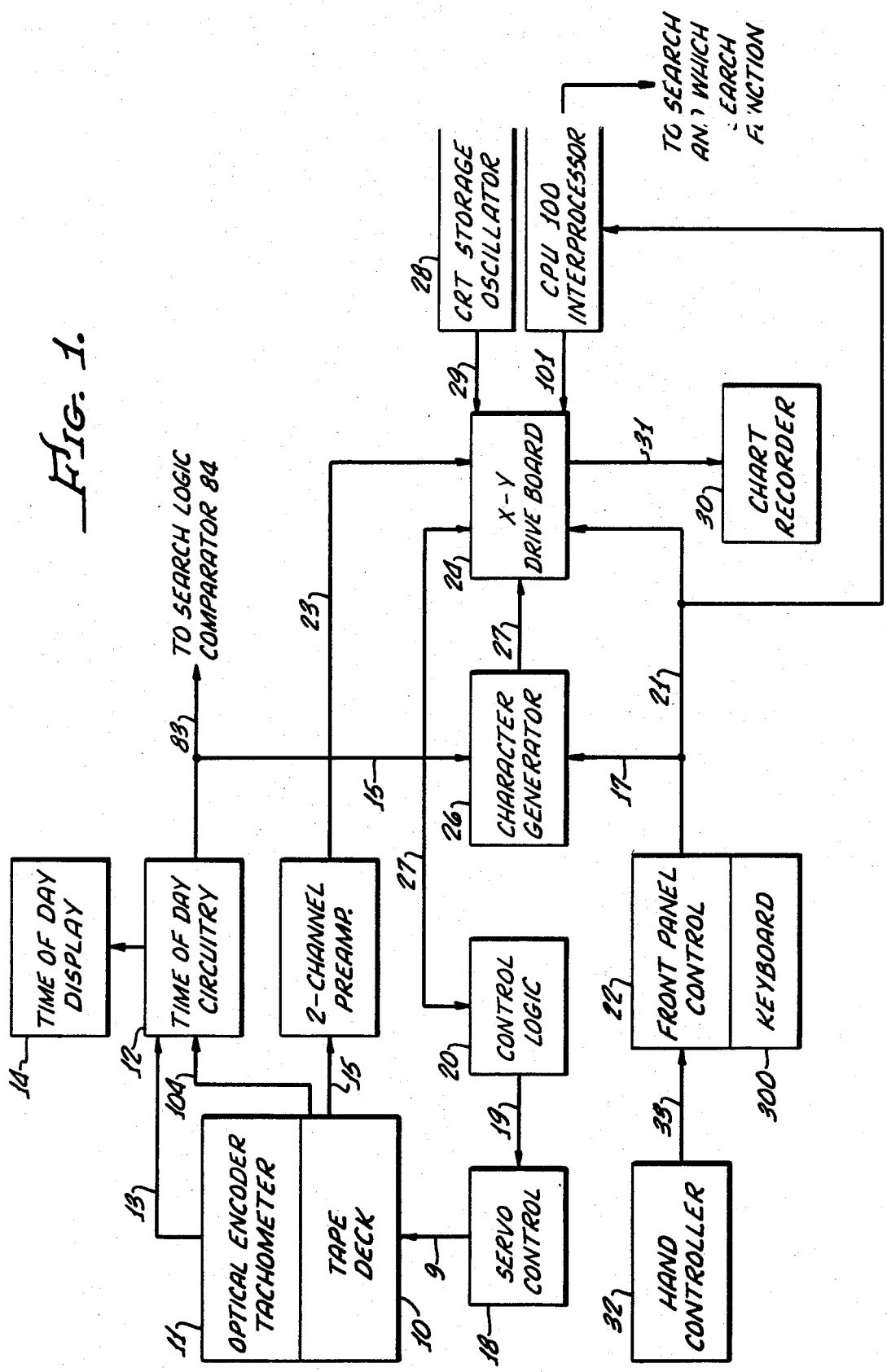
FIG. 1 is a block diagram of the overall system organization.

Referring to the drawings, FIG. 1, shows an overview of the components comprising the invention which include a tape Deck 10 for reading prerecorded ECG signals; an optical encoder Tachometer 11 (which is preferable a component of the tape deck) for generating an Output 13 indicative of the tape velocity; a time of day Circuit 12 responsively connected to the Output 13 of the optical encoder Tachometer 11 for determining the time of recorded events as measured from an encoded signal at the beginning of the tape, or as entered manually when the tape deck is started; a time of day Display 14 responsively connected to the time of day Circuitry 12 which continuously indicates the real "time" of the event then being read by tape Deck 10. Tape Deck 10 is controlled by Servo 18 which in turn is responsive in part to Inputs 21 from a front panel Control 22 that are generated by operator commands as more fully described herein below. The signal Output 15 of the tape Deck 10 is coupled to a two-channel Preamplifier 16, which conditions the signals for utilization in accordance with the processing circuitry also as more fully described herein below:

The time annotations, character annotation (such as patient identity and file identification) and the marking of abnormal beats are implemented by the character Generator 26. Character Generator 26 receives Inputs 15 from the time of day Circuitry 12, as well as Inputs 17 from the front panel Control 22. The Output 27 of character Generator 26 is coupled to the X-Y drive Board 24, which also receives input Signals 21 from the front Panel 22, and from Output 23 of the two-channel Preamp 16. Character Generator 26 includes its own programs in the form of data PROMS (programmable read only memories) for generating the appropriate alphanumeric markers. The "X", "Y" and "Z" signals required to write a particular character or annotation are generated by a dot matrix encoder in combination with D/A convertor circuitry, the details of which are well known in the prior art, and are not included herein as they form no part of the present invention. The sweep signals generated by the character generator are independent of those generated by the X-Y drive Board 24 except to the extent that these signals constitute one input to the X,Y deflection circuitry as more fully described below:

The X-Y drive generates the appropriate cartesian sweep deflections in response to the display format as selected on the front Panel 22 by the operator, and in accordance with the character Generator 26, all in coordination with the two-channels of ECG Data 23 from the two-channel Preamp 16. The synthesized X-Y Output 29 is coupled to storage Oscilloscope 28 for display. The positioning of the tape Deck 10 and the reading of information stored on the tape is controlled by servo Logic 18, which is responsively coupled as indicated by the Numeral 27 to the X-Y drive Board 24. The reading of the tape recorded data for display is thus indirectly controlled by the Output 27 of the X-Y drive board. Servo 18 converts the Output 19 of control Logic 20 into power signals which operate tape Deck 10 via Line 9. Thus upon selection of the display format and time of day by the operator via front panel Control 22, the X-Y drive Board 24 will cause the tape deck to run either forward or backward until the tape record is positioned at the selected start time, at which point the tape deck will be actuated to read data (via Line 15, two-channel Preamp 16, X-Y drive Board 24, and Output 29) so as to trace the selected portion of a recording on the screen of CRT storage Oscilloscope 28. When the screen is full (i.e., a specified amount of real time data is traced and displayed as a predetermined number of horizontal data lines each having a predefined real time length) in accordance with the particular format selected, the X-Y drive Board 24 will Output on 27 a stop signal which causes appropriate responses to be generated (via 20, 19, 18 and 9) to halt tape Deck 10. The output 31 of the X-Y drive Board 24 may also be coupled to a conventional chart Recorder 30 in a data format compatible therewith and in accordance with the selected display format chosen by the operator.

Figure 2:
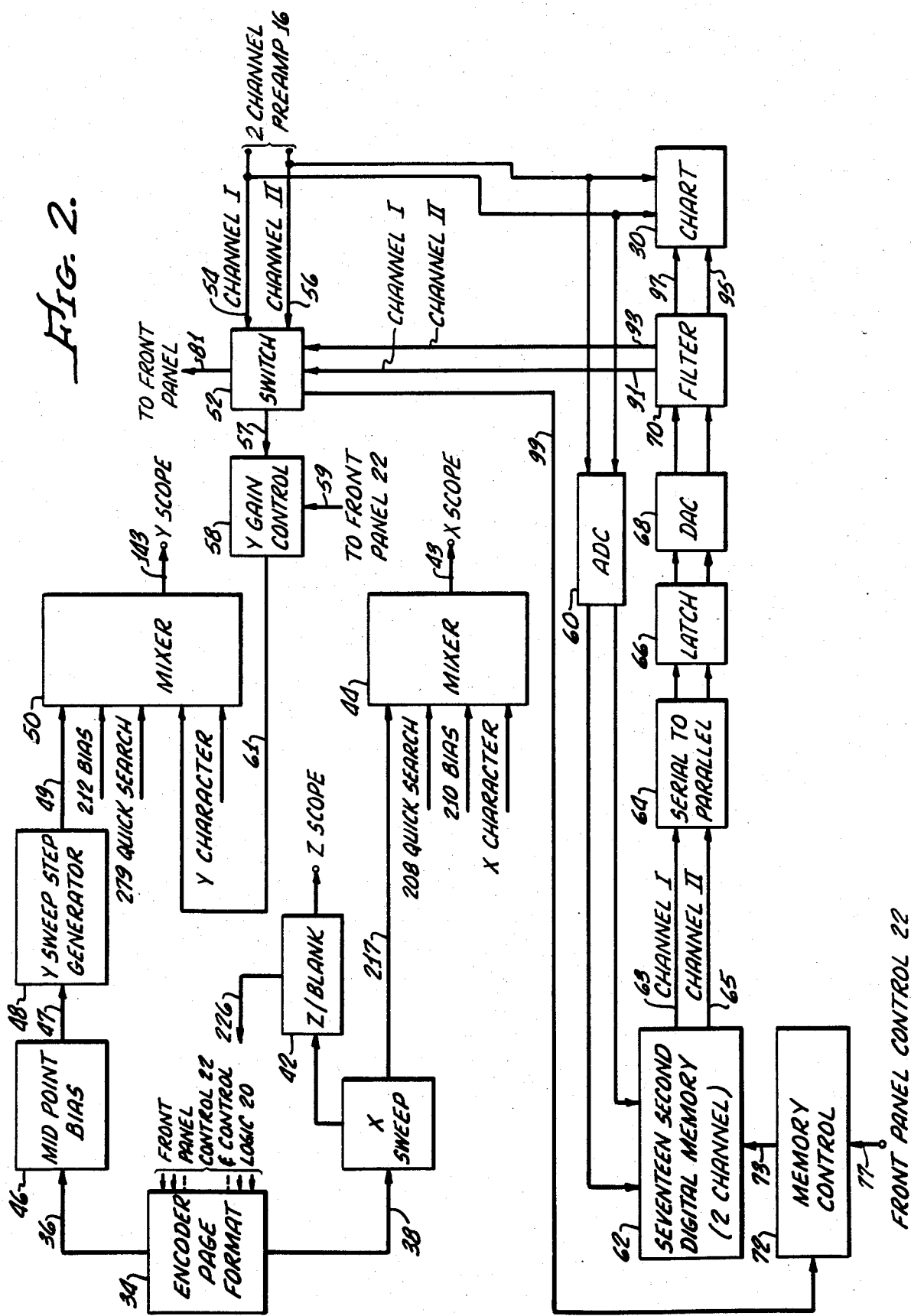
FIG. 2 is a functional block diagram of the X-Y circuit board.

FIG. 2 illustrates the salient features of the circuitry included within the X-Y drive Board 24, specifically a page format Encoder 34 (having a plurality of inputs coupled to the front panel control and control Logic 20) for translating particular display commands into a format array comprising appropriately coded "y" and "X" axis signals on Busses 36 and 38 respectively. The binary coded signals on Bus 38 provide the input to the "X" sweep Circuit 40. The output of "X" sweep Circuit 40 is coupled to a "Z" blanking Circuit 42 which senses, from the output of the "X" sweep Circuit 40, when the end of the line (limit of the "X" deflection) has been reached, at which point the beam is blanked by 42 during the retrace sweep to the left side of the cathode-ray storage Tube 28. The Output 217 of the "X" sweep Circuit 40 is coupled to Mixer 44 which is used to modify the signal generated by "X" sweep Circuit 40 in accordance with a designated bias Input 210 and inputs selected by CPU 100 (such as the "X" portion of the Output 27 from character Generator 26). The Output 43 of Mixer 44 is the "X" deflection voltage for Oscilloscope 28. Similarly, Bus 36 is connected to a midpoint bias Circuit 46 which automatically determines the vertical midpoint of the Y axis sweep regardless of the number of steps in the vertical direction which may be displayed on the cathode-ray storage Tube 28. The Output 47 of the midpoint bias Circuit 46, is coupled to a Y sweep Circuit 48, and the Output 49 of the Y sweep Circuit 48 is coupled to Mixer 50 wherein Bias 212 and inputs selected by CPU 100 (such as "Y" character drive signals from Output 27 of character Generator 26 or quick search Input 209) are mixed to produce the "Y" deflection voltage for storage Oscilloscope 28.

The magnetic tape data is typically ECG signals from two spatially separated electrodes, each having its own importance to the clinical analyst. Both signals are amplified by Preamp 16; the Channel I data is communicated via Line 54 and the Channel II data is communicated via Line 56. Lines 54 and 56 are connected to Switch 52 and to analog-to-digital Convertor 60. The Switch 52 selects either Channel I or Channel II for display, the selected channel being outputted on Line 57 to the input of the "Y" axis gain Control 58. The "Y" gain control Circuit 58 is responsively coupled Via 59 to the front panel Control 22—so that the magnitude of the "Y" sweep of each vertical step is appropriately scaled according to the operating mode and display format chosen by the operator. The Output 61 of gain control Circuit 58 is applied as data to one of the inputs to Mixer 50.

The system also has the capability of providing for hard copy output on chart Recorder 30. Analog data from Channels I and II are converted to digital serial format information for storage by Memory 62. The digital Memory 62 can be of sufficient capacity to store 60-minutes of real time data on each channel for subsequent random access, or it may only have sufficient capacity to store a small segment of data for subsequent display and analysis. For the purpose of the present invention, a memory capacity sufficient to store 17-seconds of two-channel real time data is deemed adequate.

The Outputs 63 and 65 corresponding to Channel I and II data respectively are converted by the serial to parallel Convertor 64 into binary words representative of the instantaneous amplitudes of each sample element of the waveforms as digitalized by the analog-to-digital Convertor 60. The binary words are stored in Latch 66 (which is typically an 8-bit flip-flop register). A digital-to-analog Convertor 68 converts the information held within Latch 66 into analog form. The output of Latch 66 is filtered by Filter 70 to reduce the high frequency components introduced by the sampling process, and applied to the Inputs 95 and 97 of chart Recorder 30 for hardcopy print out. The output of Filter 70 is also connected to Switch 52. When the 17-second display is selected, Switch 52 functions to first select for input to "Y" gain Control 52 the Channel I data on Line 91. Thereafter, Switch 52 selects the Channel II data on Line 93 and initiates a reread of digital Memory 62 via communication Link 99 and Memory Control 72. The subsequently selected Channel II data on Line 92 is then displayed on alternate rows of CRT storage Oscilloscope 28 with the original Channel I data.

The memory Control 72 is coupled to Memory 62 and to the front panel Control 22 as indicated by the Numbers 73 and 77. The memory Control 72 selectively causes a portion of the Memory 62 to be read and displayed on Scope 28 and/or chart Recorder 30 in response to command signals from front panel Control 22 initiated by the hand Controller 32. Digital circuitry within the memory Control 72 generates the proper commands to serially read out Memory 62 for ultimate display of a desired data segment.

Figure 3:
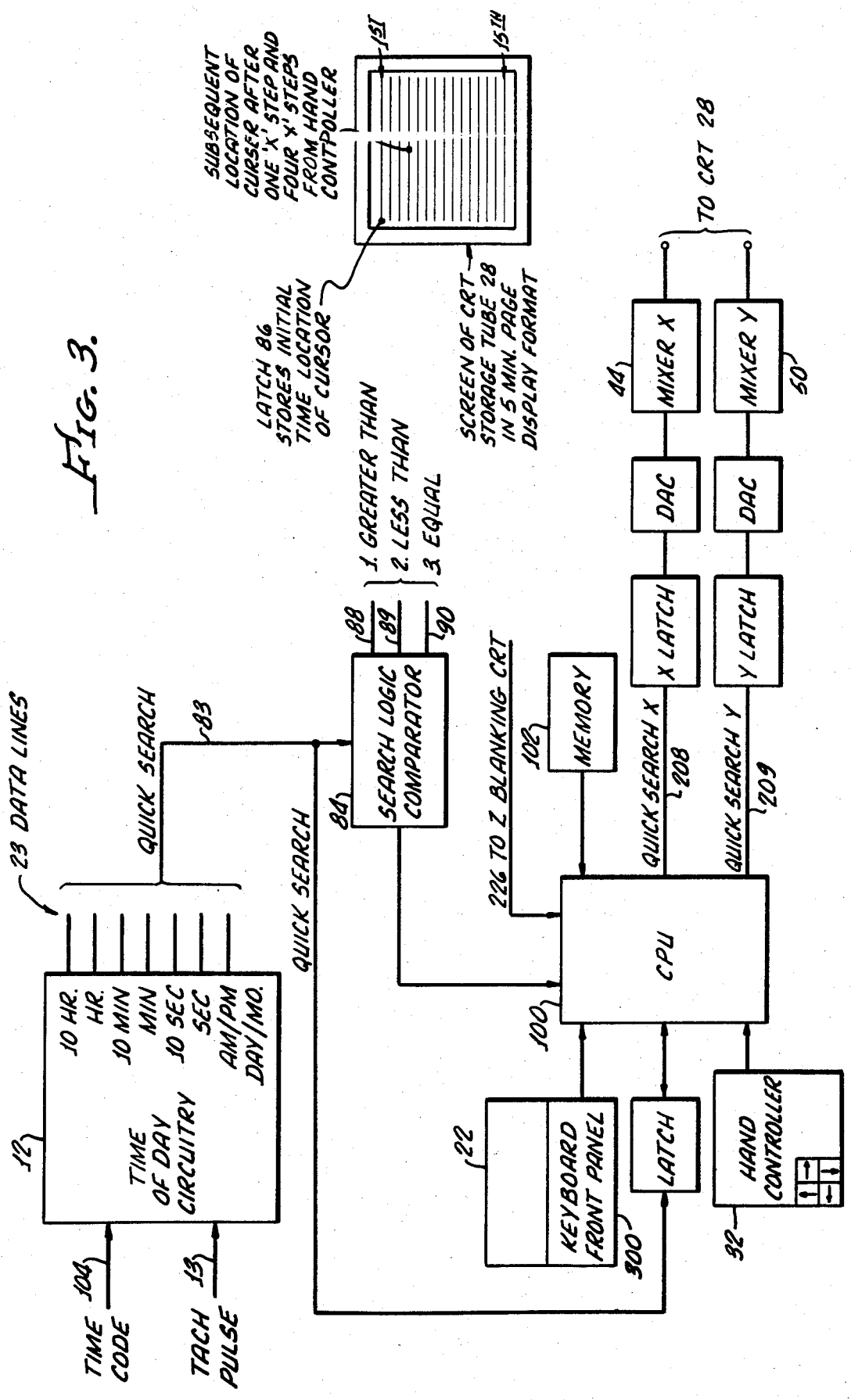
FIG. 3 shows a block diagram of the search logic.

Referring to FIG. 3, the elements of the search logic are as follows: The line address which represents the beginning point of the desired display is entered into CPU 100 via Keyboard 300 as the time of day corresponding to the data line of interest. CPU 100 stores this number in a static Memory 102 (typically a RAM semiconductor memory) for subsequent comparison with the tape position on tape Deck 10. It will be understood that the data tape will contain coded signals which were added during the data recording phase to identify the real time, by hour and minute, which corresponds to tape position. These one-minute signals are transmitted on Line 104 to update the time of day Circuitry 12. Time of day Circuitry 12 generates, in BCD, the exact time corresponding to the instantaneous position of the data being read from the tape as updated by Tachometer signals on 13 (which increment or decrement the prerecorded one-minute tape signals on 104 depending upon the direction of the tape travel). The output Signal 83 comprises 23-lines from a 24-bit register (two-bits to code tens-hour digit (0,1,2), four-bits to code the units hour digit (0–9), three-bits to encode the tens-minute digit (0–5), four-bits to encode the units minute digit (0–9), three-bits to encode the tens-second digit (0–5), four-bits to encode the units seconds digit (0–9) and three-bits to designate A.M. and P.M. and day number). These 23-lines identified by the Numeral 83 are connected to Comparator 84 and to Latch 86. The Output 87 of CPU 100 will also consist of 23-lines which are connected to Comparator 84. When the numerical value of the time represented by the 23 data Lines 87 is greater than the numerical value of the time represented by the 23 data Lines 83, the logic signal on Line 88 will be true causing the tape control Logic 20 to run the tape deck in the forward direction. Similarly, when the Output 84 is greater than 87, Line 89 will be logically true, and control Logic 20 will cause the tape deck to run in reverse. When the two "times" are equal (the 23-bits on 87 and 84 are identical) Line 90 will be logically true and Control 20 will stop the tape Deck 10. The tape deck will then proceed to run in the forward direction so as to read out five-minutes of real time data which is contemporaneously formatted by Encoder 34 as previously described. The real time data display from Channel I or II (depending upon the state of Switch 52 as controlled through communication Link 81 via front panel Control 22) will be read out and appropriately amplified and biased via "Y" gain Control 58 and Mixer 50 for display on CRT storage Tube 28. When the display is complete, the register in Latch 86 will still contain the beginning of the five-minute page and the tape will have been advanced and stopped at the real time position corresponding to the end of the five-minute page.

FIG. 5 shows the actual circuitry used to generate and refresh the marker symbols. Program Counter 436 is initiated and terminated via sync Circuitry 438, in accordance with input signals on Line 13 from the output of Tach 11. The X, Y and Z outputs of the marker generator are thus synchronized and coordinated with the reading of ECG data from tape Deck 10 as determined by the state of switches 442 and 446, which in time are controlled by signals from state circuit 440 as more fully described herein below.

Program Counter 436 steps through each sequential address in memories 448 and 450. Where abnormal waveforms have been detected, by the arrhythmia Computer 500, the appropriate memory addresses will contain a binary word indicative of the particular abnormality symbol that is to be written adjacent to the abnormal waveform of the display. In the embodiment shown, VE type beats (typically wide, premature beats with excessive amplitudes) are stored in Memory 448, and SVE type beats (typically narrow beats more than 33% premature) are stored in Memory 450. Each of the memory addresses in Memories 448 and 450 corresponds to a point on the display screen of CRT storage Tube 28, according to the display format. When the ECG data is initially read from tape Deck 10, state Circuit 440 will be in the write mode and the arrhythmia Computer 500 will detect each heartbeat, determine whether or not it is abnormal, and then categorize the type of abnormality if one exists. A VE signal or an SVE signal will be generated by arrhythmia Computer 500 and loaded into either Memory 448 or 450 respectively at the appropriate location as determined by program Counter 436. After one full screen of display data has been read from tape Deck 10, Memories 448 and 450 will contain zeros and ones. "Zero" is arbitrarily chosen to signify a normal beat and "one" is chosen to indicate an abnormal (either ventricular ectopic or superventricular ectopic) event.

During the read mode, state Circuit 440 will cause program Counter 436 to step through each address in sequence. The output of Memories 448 and 450 are tested via Circuit 452 to determine whether or not a "one" is being outputted. When a "one" is detected, state Cicruit 452 generates a stop signal which holds program Counter 436. A command signal is then issued by test Circuit 452 via Line 489 to character generator Subassembly 454 which generates a predetermined marker symbol on display Screen 28. For example, in the case of a ventricular ectopic event, the marker symbol "VE" will be traced adjacent to the ventricular ectopic abnormal beat displayed on the screen, and an "SVE" marking symbol will be traced adjacent to superventricular ectopic abnormal beats.

Character generator Subassembly 454 is similar to prior art character generators, and are well known in the art. The character Generator 454 includes its own program counter and data PROMS for generating the appropriate alphanumeric markers. The X, Y and Z signals required to trace the marker characters are produced by a dot matrix encoder in a combination with digital-to-analog convertors and counters. Accordingly for purposes of clarity the character generator Subassembly 454 has been shown only in simplified block diagram form and that its internal organization may be constructed according to well known principles.

The overall X and Y sweep of the marker generator of FIG. 5 is independent of the X and Y sweep of the annotation character and X-Y drive Board 24 described in connection with FIG. 2. Therefore, program Counter 436 is coupled to digital-to-analog Convertors 456 and 458 whose output in turn may be coupled through conventional signal conditioning circuitry (not shown) respectively to an X-sawtooth Generator 464 and a Y-sawtooth Generator 466 respectively. Sawtooth generators 464 and 466 generate the overall X and Y drive signals for Scope 28 with respect to the marker symbols that determine the center position on the display where the marker character will be traced. The actual fine control of the trace to paint the marker character "VE" or "SVE" is accomplished by the Inputs 490 and 491 to sawtooth Generators 464 and 466 from the output of character generator Subassembly 454.

The block diagram of FIG. 5 in combination with the previously described elements of FIGS. 1-3 illustrate the relationship of the present invention with respect to the overall system. ECG data is traced on the scope Display 28 in a three-pass operation. During the first-pass or first-time interval, the ECG waveform data is traced on the display of storage Oscilloscope 28 by the X and Y sweep circuitry included within X-Y drive Board 24 of FIG. 2. On a second-pass or second-time interval, the annotation characters (such as time of day and patient information) are generated by 26 and traced on the display of the storage Oscilloscope 28. During a third-pass or third-time interval, the abnormality markers are appropriately positioned on the display next to abnormal events in the ECG waveforms by the circuitry of FIG. 5.

After the marker symbols are written and the program Counter 436 has stepped through Memories 444 and 446, the screen will contain data waveforms, time and patient annotations and abnormal marking symbols. A 60-minute display formatted with 30-lines of two-minutes each for a patient exhibiting both VE and SVE complexes may appear as shown in FIG. 4. As evidenced by the data density, the identification and recognition of the abnormality markers may be somewhat strenuous if the clinical analysis is called upon to review a large number of frames over a relatively long period of time. In order to quickly locate the SV and SVE markers from the background data, the present invention provides an enhancement system which causes the abnormality marker to blink—thus making them easily discernable relative to the constant background intensity of the data.

Referring to FIG. 5, it will be seen that all of the information necessary to rewrite the abnormal markers is contained in Memories 448 and 450. Accordingly, it is only necessary to reset program Counter 436 via reset Circuit 600 to return the program Counter 436 to its initial state at the completion of each abnormal marker writing phase. The continuous rewriting of the abnormal symbols thus provides a cyclical brightening and dimming effect at a periodic rate which is directly dependent upon the clock Rate 444 and inversely dependent upon the number of memory addresses (capacities of memories 448 and 450).

In certain cases it is advantageous to highlight only one type of marker—e.g. either the "VEs" or "SVEs". For this purpose, inhibit Gates 998 and 999 are added so to provide additional flexibility. Thus, when push button Switch 609 is depressed so as to cause program Counter 436 to reset, Switch 779 may be closed, thus inhibiting the output from Gate 998 so to prevent "VE" markers from being refreshed. Similarly, Switch 789 may be closed to inhibit the output from Gate 999 so as to prevent "SVE" markers from being refreshed.

Although the invention has been shown and described in connection with a particular application, namely that of highlighting particular ECG abnormality markers, it will be understood that the invention is not limited thereto, and that numerous changes, modifications and substitutions may be made without departing from the spirit of the invention.

What is claimed is:

1. A physiological display system comprising:
    a CRT storage tube adapted to display real time physiological events in cartesian array format;
    computer means for identifying abnormal waveforms;
    memory means responsively connected to said computer means for storing the location of abnormal waveforms relative to real time location on said CRT storage tube;

character generating means responsively coupled to said memory means for producing a marker to identify at least one type of abnormal waveform;

program counter means coupled to said memory means for reading memory locations in synchronism with the real time which corresponds to the X-Y location of the waveform on said CRT storage tube;

X-Y sweep deflection means responsively coupled to said character generating means for writing the markers generated by said character generating means on said CRT storage tube;

refreshing means responsively connected to said program counter means and said character generating means for returning said program counter means to its initial state and for causing said program counter means to continuously recycle through each successive memory location whereby said character generation means will rewrite abnormality markers periodically so as to cause such markers to be distinguished from physiological data which is not periodically refreshed.

2. In an electrocardiographic display system of the type employing a CRT storage tube, the improvement which comprises:

arrhythmia computer means for identifying a first type of abnormal ECG waveform;

first memory means responsively coupled to said arrhythmia computer means for storing the location of first type abnormal ECG waveforms relative to their location on the CRT storage screen;

character generating means responsively coupled to said first memory means for producing abnormal waveform markers on the CRT storage screen;

program counter means coupled to said first memory means for causing the contents of successive memory locations to be read;

CRT sweep deflection means responsively coupled to said character generating means and said program counter means for writing markers on the CRT storage tube screen; and means for selectively refreshing first type markers written on the CRT screen so as to cause first type markers to be distinguishable from ECG waveforms and nonrefreshed markers.

3. The apparatus recited in claim 2 wherein said arrhythmia computer means is adapted to also identify a second type of abnormal ECG waveform, and wherein is included:

second memory means responsively coupled to said arrhythmia computer means for storing the locations of a second type of abnormal ECG waveforms relative to their locations on the CRT storage screen;

means for coupling the output of said second memory means to said character generating means;

means for coupling the output of said counter means to said second memory means whereby the contents of said second memory means will be read; and means for selectively refreshing second type markers written on the CRT screen so as to cause the second type markers to be distinguishable from the ECG waveforms and other types of markers when said second type markers are selected and no other type of markers are selected.

4. The apparatus recited in claim 3, wherein is included:

means for selecting first type and second type markers simultaneously whereby both types of markers will be distinguishable from ECG waveforms.

5. The apparatus recited in claim 3 wherein said means for refreshing markers comprises:

means for causing said program counter to reiterate the counting sequence following completion of each counting cycle.

6. In a system for displaying physiological signals on a storage tube display, said signals being reproduced at a rate substantially greater than the rate at which said signals occurred in real time, the improvement which comprises:

detector means for identifying particular physiological events according to predetermined criteria;

marking means responsively coupled to said detector means for marking identified events so as to distinguish each type of physiological event identified from every other type of physiological event identified;

memory means responsively coupled to said detector means for storing the time location of identified physiological events;

means responsively coupled to said memory means for selectively refreshing particular types of identifying event markers as to cause a particular type of marker to be distinguishable from other types of event markers and data.

7. The apparatus recited in claim 6 wherein said means for identifying particular physiological events comprises an arrhythmia computer.

8. The apparatus recited in claim 7 wherein said means for marking identified events comprises:

synchronization and state circuitry means for conforming the position of the markers to the corresponding real time position on the display;

program counter means having its input responsively coupled to said synchronization and state circuitry means for counting and initiating execution of display steps;

a plurality of memories means each responsively coupled to the output of said program counter means for storing digital words indicative of a particular type of physiological event as determined by said arrhythmia computer;

test circuit means coupled to the outputs of each of said memories for determining if the address specified by said program counter means contains an identified event;

interrupt means responsive to said test circuit means for generating a stop signal to temporarily halt said program counter means if said address contains a detected event;

character generating means for generating a marker to indicate the type of identified physiological event;

deflection means responsively coupled to said character generating means for producing markers.

9. The apparatus recited in claim 8 wherein said means for selectively refreshing particular types of event markers comprises:

means for causing said program counter means to repeatedly sequence through each address of each of said memory means.

* * * * *